United States Patent [19]

Perucho et al.

[11] Patent Number: 4,725,550
[45] Date of Patent: Feb. 16, 1988

[54] NOVEL MUTATION OF THE C-K-RAS ONCOGENE ACTIVATED IN A HUMAN LUNG CARCINOMA

[75] Inventors: Manuel Perucho, Stony Brook; Hirofumi Nakano; Fumiichiro Yamamoto, both of Port Jefferson Station; Craig Neville, Miller Place, all of N.Y.

[73] Assignee: Research Foundation of State University of New York, Albany, N.Y.

[21] Appl. No.: 572,694

[22] Filed: Jan. 19, 1984

[51] Int. Cl.$^4$ .................. C12N 1/00; C12N 15/00; C12P 21/00; C07H 15/12
[52] U.S. Cl. .................................... 435/320; 435/68; 435/70; 435/172.3; 435/235; 536/27; 935/9; 935/66
[58] Field of Search .................. 435/68, 317, 172.3, 435/235; 935/1, 9, 22; 536/27

[56] References Cited

U.S. PATENT DOCUMENTS 4,535,058  8/1985  Weinberg et al. .................. 435/6

OTHER PUBLICATIONS

Taparowsky et al, 1983, "Structure and Activation of the Human N-ras Gene", *Cell*, v34, 581–586.
Rein et al, 1985, "Mutational Activation of Proto-Oncogenes", *Molecular Basis of Cancer, Part A* . . . , pp. 357–368, Alan R. Liss, Inc.
Notario et al, 1984, "A Common Mechanism for Malignant Activation of ras Oncogenes in Human Neoplasia . . . ", *Cancer Cells*, v2, 425–432.
Nakano et al, 1984, "Structure and Mechanisms of Activation of the ci-ki-ras Oncogene . . . ", *Cancer Cells*, v2, 447–454.
Kraus et al, 1984, "A Position 12-Activated H-ras Oncogene in all HS578T Mammary Carcinosarcoma Cells but not Normal Mammary Cells . . . ", *PNAS*, v81, pp. 5384–5388.
Sekiya et al, 1984, "Molecular Cloning and the Total Nucleotide Sequence of the Human c–Ha–ras–1 gene . . . ", *Proc. Natl. Acad. Sci.*, v81, 4771–4777.
Nakano et al, 1984, "Isolation of Transforming Sequences of Two Human Lung Carcinomas: Structure and Functional Analysis . . . ", *Proc. Natl. Acad. Sci.*, v 81, pp. 71–75.
Shimizu et al, 1983, "Three Human Transforming Genes Are Related to the Viral ras Oncogenes", *Proc. Natl. Acad. Sci.*, v80, pp. 2112–2116.
Der et al, 1982, "Transforming Genes of Human Bladder and Lung Carcinoma Cell Lines are Homologous . . . ", Proc. Natl. Acad. Sci., v79, 3637–3640.

*Primary Examiner*—Thomas G. Wiseman
*Assistant Examiner*—Stephanie Seidman
*Attorney, Agent, or Firm*—Omri M. Behr

[57] ABSTRACT

A c-Kirsten ras oncogene has been isolated from a human lung tumor cell line. This c-Kirsten ras has a mutation in codon 61 of the second coding exon and is capable of transforming NIH/3T3 mouse fibroblast cells to tumorigenic cells.

18 Claims, No Drawings

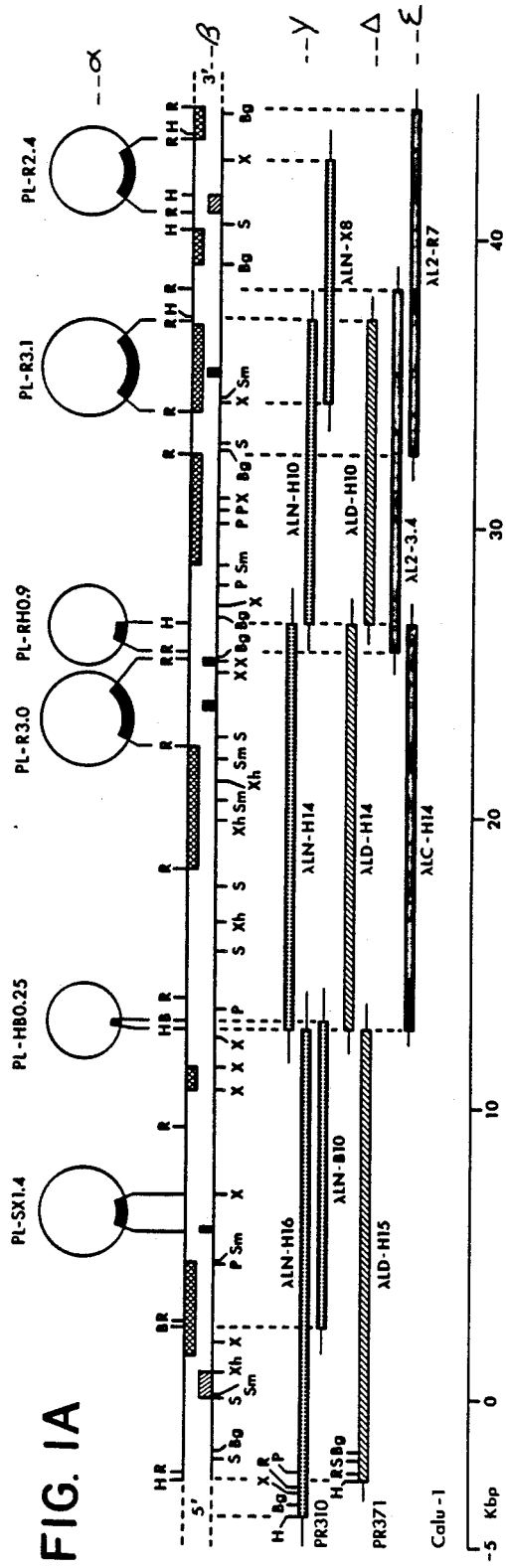
FIG. 1A
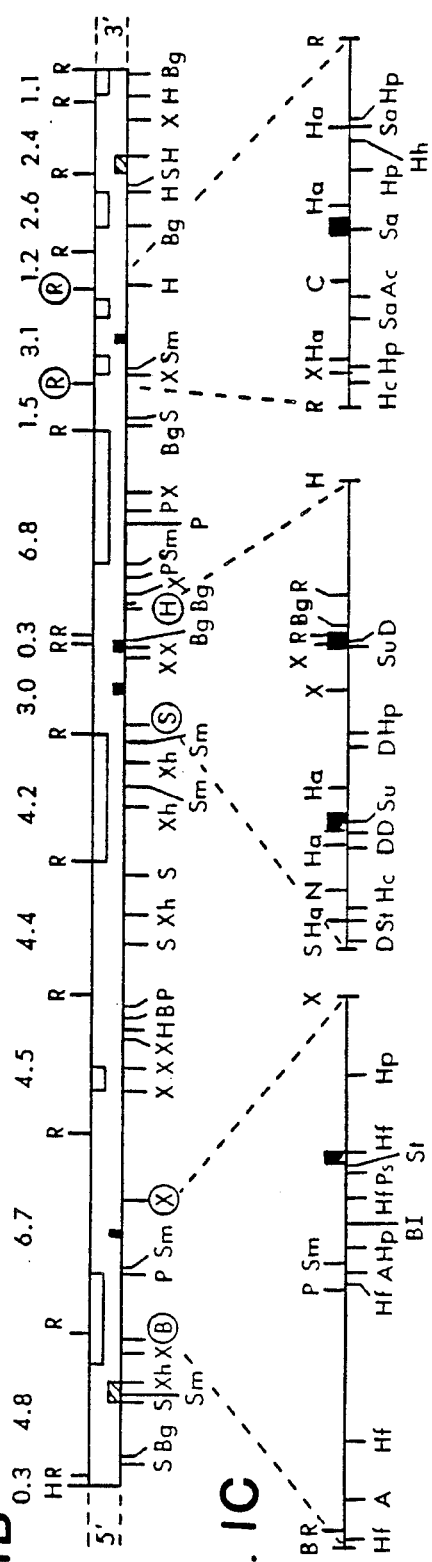
FIG. 1B
FIG. 1C

FIG. 3

Pin III-A2-PR310 exon 2

NOVEL MUTATION OF THE C-K-RAS ONCOGENE ACTIVATED IN A HUMAN LUNG CARCINOMA

BACKGROUND OF THE INVENTION

It has previously been shown that some human tumor cells contain oncogenes derived from activated protooncogenes which are believed to play an important role in the origin, progression or maintainence of these tumors. Identification of these oncogenes in a physiological system would be a useful diagnostic tool in the identification or detection of their respective tumor systems.

The oncogenes activated in certain human tumors whose DNA is able to morphologically transform the mouse NIH/3T3 fibroblasts have been found to represent members of the ras gene family. The ras genes are eukaryotic genes encoding for immunologically related proteins of 21.000 MW (p21) which were initially found in the genome of certain animal RNA tumor viruses, in particular, the viruses of Harvey and Kirsten. The human gene homologue to the oncogene of the Harvey virus (c-H-ras) has been found activated in some tumor cell lines derived from bladder carcinomas and lung carcinomas. The oncogene of other tumor cell lines derived from neuroblastomas (the SK-NS-H cell line), leukemia and other types of cancer, has been identified as another member of the ras family and has been named N-ras.

The oncogene originally found in certain colon (the SW480 and SK-CO-1 cell lines) and in certain lung (the Calu-1 and SK-LU-1 cell lines) carcinomas, which has been posteriorly found in a broad range of human tumors is the human homologue of the Kirsten virus oncogene (c-K-ras).

The mechanisms by which these oncogenes have been activated from their corresponding protooncogenes in these human tumors has been established as point mutations in their protein coding regions (exons). Thus, the c-H-ras oncogene present in the T24 bladder carcinoma cell line has been activated by a single base substitution at position 12 of the first coding exon (Capon, et al., (a) *Nature*, 302, 33 (1983); Tabin, et al., *Nature*, 300, 143 (1982); Reddy, et al., *Nature*, 149 (1982); Taparowsky, et al., *Nature*, 300, 762, (1982) which results in the substitution of glycine by valine in this position of the P21 protein. The oncogene of the Hs242 lung carcinoma cell line has been activated by a mutation in the second coding exon, at position 61, which results in the substitution of glutamine by leucine (Yuasa, et al., *Nature*, 303, 775 (1983).

The N-ras oncogene present in the SK-NS-H neuroblastoma cell line has been activated by a base substitution at position 61 of the second exon which results in the substitution of glutamine by lysine (Taparowsky, et al., *Cell*, 34, 581–86 (1983).

The c-K-ras oncogene present in the Calu-1 cell line has been activated by a point mutation at position 12 of the first exon which results in the substitution of glycine by cysteine (Shimizu, et al., *Nature*, 304 497 (1983), Capon, et al.(b), *Nature*, 304, 507, 1983b)). The c-K-ras oncogene present in the SW480 colon carcinoma cell line contains a mutation at the same position 12 which results in the substitution of glycine by valine (Capon, et al. (b), supra (1983).

Prior to the work leading to the present invention, no mutations have been found or identified in c-K-ras oncogenes other than codon 12 of the first exon.

SUMMARY OF THE INVENTION

Starting with two human lung tumors designated PR310 and PR371 in the tumor collection maintained at the Sloan-Kettering Institute, Rye, N.Y., by J. Fogh, which have been maintained in nude mice, mutated human Kirsten oncogenes (c-K-ras) have been detected and isolated by their ability to induce morphological transformation of NIH/3T3 mouse fibroblasts. Sequences of approximately 40 kilobase pairs of the c-K-ras oncogene have been isolated and the mutations responsible for their activation in the PR310 and PR371 tumors have been identified. The oncogene present in the PR371 tumor presents a mutation in position 12 of the first coding exon which results in the substitution of glycine by cysteine, being therefore the same mutation as the mutation which activated the oncogene present in the Calu-1 cell line (Shimizu, et al., 1983, supra, Capon, et al. (b), 1983, supra).

The oncogene present in the PR310 tumor has been activated by a point mutation at position 61 of the second coding exon. This mutation results in the incorporation of histidine in place of the glutamine present at this position in the c-K-ras protooncogene as well as in the oncogenes of the Calu-1, SW480, and PR371. Therefore, this mutation which results in the activation of the c-K-ras oncogene in PR310 tumor is a novel mutation not heretofore described. It has further been shown that this activation is the result of a single base change in the second coding exon, namely, an A→T (adenine to thymidine), transversion in the third base of codon 61 of the encoded P21 protein.

BRIEF DESCRIPTION OF THE DRAWINGS

FIG. 1 is a series of restriction maps of the c-K-ras oncogene:

(a)
- (α) The location of certain detecting plasmids,
- (β) abreviated restriction map,
- (γ) major Hind III, Bam HI and Xba I fragments of PR310 oncogene cloned in phage vectors,
- (δ) major Hind III, Bam HI and Xba I fragments of PR371 oncogene cloned in phage vectors,
- (ε) major fragments of Calu-1 oncogene cloned in phage vectors.

(b) Exploded version of (a) β.

(c) Exploded version of (b) showing sectors containing the exons.

FIG. 2 is a blot of electrophoresed 3T3 transformant DNA after restriction enzyme digestion hybridized with different cloned oncogene fragments as probes.

Figure 3:
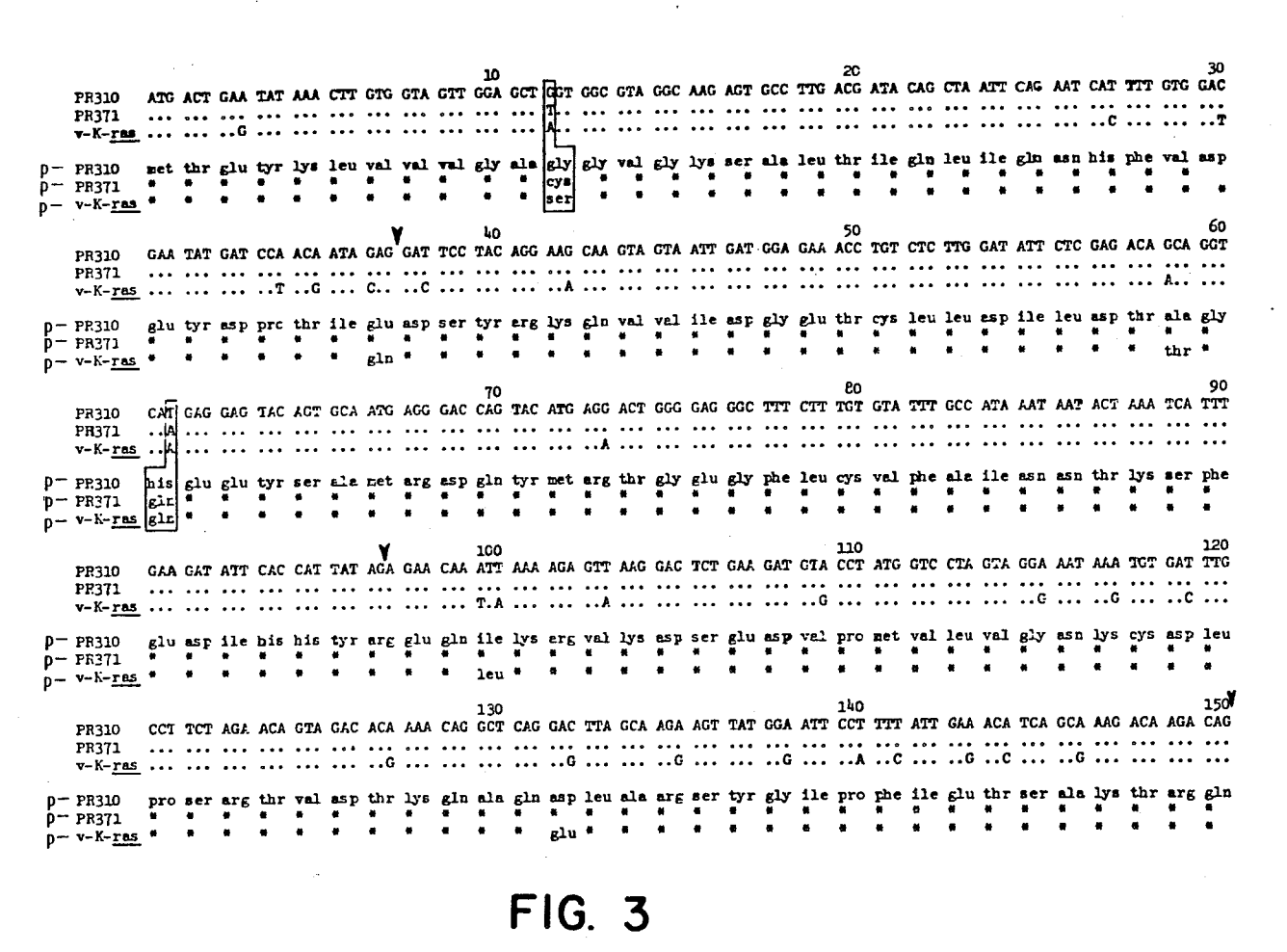

FIG. 3 is a partial nucleotide codon/protein sequence relative to the P21 protein encoded by the PR310, PR371 and v-K-ras oncogenes showing location of the splicing signals of the 1st, 2nd and 3rd exons and the oncogenic mutations of the 1st and 2nd exons.

Figure 4A:
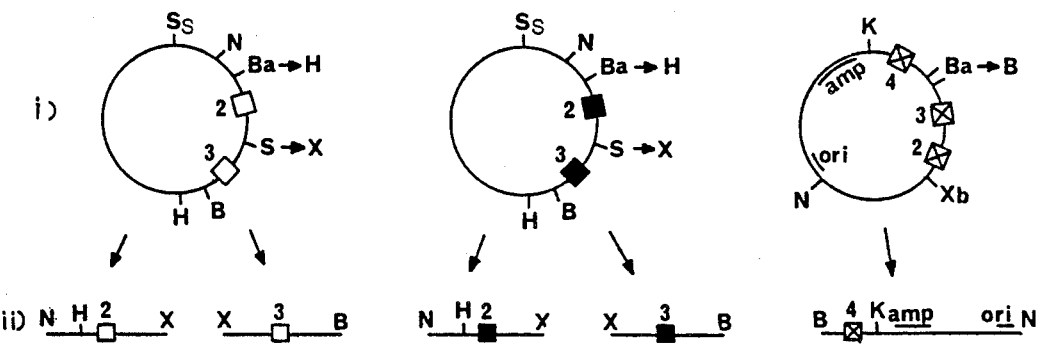

FIG. 4 depicts the chimeric plasmids constructed to demonstrate the oncogenic potential of the mutation of the second exon of PR310 oncogene.

(Ai) shows the original plasmids and rearrangement of restriction sites.

(Aii) shows the purified DNA fragments containing the exons of the c-K-ras and c-H-ras oncogenes.

(Bi) shows the recombined 2-4 exon plasmids.

(Bii) shows the purified DNA fragments containing the recombined exons.

(Biii) shows the purified DNA fragments containing the 1st exons of PR310 and PR371 oncogenes.

(C) shows the segments of Bii ligated to Biii and indicates the oncogenicity of the respective fragments.

Figure 5:
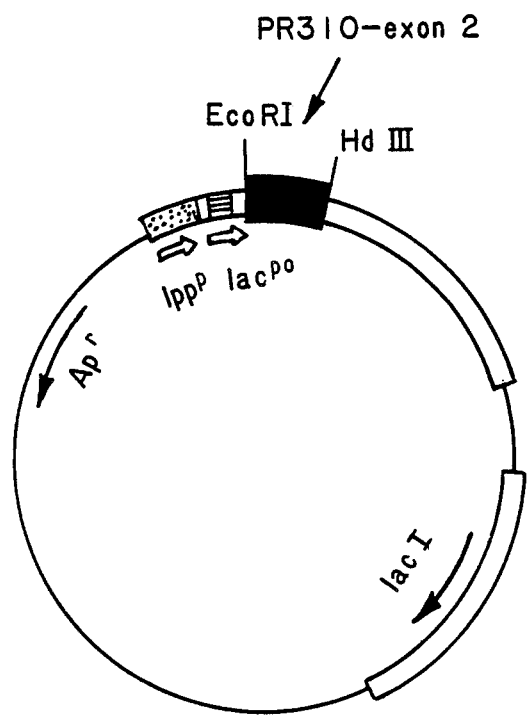

FIG. 5 is a plasmid for the expression of the polypeptide encoded by the 2nd exon.

DESCRIPTION OF THE PREFERRED EMBODIMENTS

Human tumors PR310 and 371 maintained in nude mice were obtained from the tumor collection maintained at the Sloan-Kettering Institute, Rye, N.Y., by J. Fogh. Frozen tumor tissues were blended in the presence of liquid nitrogen and the tumor lysed with proteinase K containing buffer in the presence of SDS. The crude DNA was then purified by extraction with phenol/chloroform and sized by gel electrophoresis. NIH/3T3 cells were maintained as monolayer cultures and the purified DNA from the human tumors PR310 and 371 introduced into the cell lines by means of the calcium phosphate procedure of Wigler, et al., (Cell, 16, 777 (1979)). The cells were then incubated, trypsinized and seeded into culture dishes, and grown in culture until scoring of foci at between days 14 to 21. The foci were then cloned, suitably by the use of glass cylinders. The cloned cells (primary transformants) were grown into mass culture and used to prepare DNA by the above method. One of these primary transformant cell lines containing the oncogene of tumor PR310 has been designated Suny 310-1 and has been deposited in the American Typeculture Collection under Accession No. ATCC-CRL8477. The DNA obtained from the primary transformants is retransferred into the NIH/3T3 cell culture as above and the secondary transformant DNA obtained therefrom.

If desired, this procedure may be repeated to obtain the tertiary transformants cell culture and thus tertiary transformants DNA therein.

The total DNA obtained from the secondary transformants (which contain mouse 3T3/DNA and human oncogene DNA) is then subjected to digestion with restriction endonucleases Hind III, Bam HI or Xba I and cloned into the appropriate phages, i.e., λ 47.1 (Loenen, et al., Gene, 10, 249 (1980) and λ g.t. wes λ B (Leder, et. al., Science, 196, 175 (1977)) and the recombinant phages used to infect a strain of E. coli. The incubated plates are then contacted with a nitrocellulose filter to absorb the phages, the phage heads destroyed and the appropriate fragments identified by probes substantially similar to the fragments themselves.

The oncogene DNA fragments thus cloned in recombinant phages are purified and used to determine their restriction maps which are combined to derive the entire restriction map of the c-K-ras oncogene as shown in FIG. 1. The location of the c-K-ras exons was determined by hybridization with appropriate fragments of the viral Kirsten oncogene. Thus, it was possible to locate the exons in the PR310 and PR371 oncogenes which, after location, were sequenced by the Maxam-Gilbert method, as illustrated in FIG. 3.

Comparative analysis of the sequences of the 2 first exons of the PR371 and PR310 oncogenes revealed only two differences. In the first exon, the PR310 oncogene contain a guanosine (G) in the first base of the codon 12 of the P21 protein, as determined by aligning the sequence of the oncogene with the viral oncogene (Tushida, et al., Science, 217, 937 (1982)), while the PR371 oncogene contain a Thymidine (T) at this position. The rest of the sequence is identical between the PR310 and PR371 oncogenes in this first exon. Thus, the PR310 oncogene encodes glycine at position 12 while the PR371 encodes cysteine. In the second exon, the PR310 oncogene contains a Thymidine (T) as the third base of the codon 61, determined as above, while the PR371 oncogene contains the Adenosine (A), the rest of the nucleotide sequence of the second exon being identical in these two oncogenes. The nucleotide sequence of the third exon of these oncogenes do not show any difference.

By constructing chimeric genes (FIG. 4) containing the first, second and third exons of the PR310 and PR371 c-K-ras oncogenes in all possible combinations, and the fourth exon of the c-H-ras oncogene (the gene isolated from the T24 human bladder carcinoma (Goldfarb, et al., Nature, 296, 404, (1982)) which is known to contain a mutation in codon 12 of the first exon and no mutations in the 2nd, 3rd and 4th exons (Tabin, et. al., 1982 ibid, Reddy, et al., 1982 ibid, Taparowsky, et al., 1982 ibid, capon, et al., 1983a ibid), it was possible to determine the mutational origin to the T present in the first exon of the PR371 and the T present in the second exon of the PR310 oncogenes; chimeric genes containing the first exon of the PR310 oncogene and/or the second exon of the PR371 oncogene did not show transforming activity, thus demonstrating that these oxons did not show transforming activity, thus demonstrating that these exons contain a normal nucleotide sequence that is, the sequence contained in the exons of the normal human c-K-ras protoncogene. Therefore, the inescapable conclusion of these experiments is that the T present at codon 12 in the first exon of the PR371 oncogene and the T present at codon 61 in the second exon of the PR310 oncogene were the result of mutational events. This conclusion was confirmed after the nucleotide sequence of the human c-K-ras oncogene was published (McGrath, et al., Nature, 304, 501 (1983)).

The chimeric plasmids experiment (FIG. 4) also demonstrated the oncogenic potential of the mutations present in the first and second exons of PR371 and PR310 oncogenes respectively. For example, a chimeric gene containing the 1st exon of the PR371 oncogene and the 2nd and 3rd exons of the same gene and the fourth exon of the c-H-ras oncogene, the latter all containing normal sequences, did transform the NIH 3T3 cells. This result confirmed our previous conclusion of the potential oncogenicity of the 1st exon mutation in the PR371 oncogene. Similarly, the chimeric gene containing the normal 1st and 3rd exons of PR310 oncogene, the normal 4th exon of the c-H-ras oncogene and the 2nd mutant exon of PR310 oncogene also showed transforming activity.

Therefore, the conclusion of these experiments is that:

(1) A G→T transversion of the first nucleotide of codon 12 in the first exon of the PR371 oncogene is the mutation which resulted in the activation of the c-K-ras protonocogene in this tumor.

(2) A A→T transversion of the third nucleotide of codon 61 in the second exon of the PR310 oncogene is the mutation which activated the c-K-ras protoncogene in PR310 tumor.

The first conclusion was confirmed by the publication of the nucleotide sequence of the Calu-1 c-K-ras oncogene by other workers (Shimuzu, et al., Nature, supra, 1983, and Capon, et al., (b), *Nature*, supra (1983). This oncogene contains a mutation identical to the mutation of the PR371 oncogen, i.e., a G→T transversion at codon 12 of the first exon, which results in the substitution of glycine by cysteine.

This information, that the codon 61 mutation is responsible for transformation, provides a means for determining whether a tumor taken from a patient is indeed a tumor containing a c-K-ras oncogene of this particular type, thus providing the physician with the opportunity to make the appropriate prognosis and select appropriate treatment.

Utilizing well known synthetic techniques, an appropriate number of nucleotides, say, 4 to 6 condons in length, and including therein a codon corresponding in structure to codon 61 of the PR310 DNA, is prepared and radiolabeled in the known manner to provide radioactive probes. Such probes, utilized in the conventional manner, (Conner, et al., PNAS, 80, 278, (1983)) can be used to detect a codon 61 mutation in the aforementioned tumor samples.

Another diagnostic mode is to prepare an *E. coli* expression vector containing the mutated second exon of PR310/DNA and utilizing this expression vector to prepare the appropriate polypeptide containing the correspondingly changed amino acid structure. Such polypeptides may be used to prepare monoclonal antibodies which in turn can detect the presence of the P21 protein mutated at point 61 in a tumor sample.

EXAMPLE I

DNA Preparation and Purification of DNA Fragments (a) To prepare DNA from the human tumors PR310 and 371 maintained in nude mice, frozen tumor tissues were ground in a steel Waring blender in the presence of liquid nitrogen. After the liquid nitrogen evaporated, the tumor powder was lysed with a hot (65° C.) lysis buffer containing 0.5% sodium dodecyl sulfate, 20 mM EDTA, 10 mM Tris-HCl (pH 7.5), 0.15M NaCl, and 200 µg of proteinase K (Beckman) per ml.

(b) The thus obtained crude DNA was then purified by extraction with an equal volume of a mixture of phenol, chloroform and isoamyl alcohol (25:24:1) and once more with chloroform and isoamyl alcohol (24:1) before precipitation with two volumes of absolute ethanol. The DNA precipitates were removed with a glass rod and washed successively with two changes of 70% ethanol and two changes of 100% ethanol. The precipitates were then air-dried after which they were dissolved in 1 mM Tris-HCl (pH 7.5), 1 mM EDTA at a DNA concentration of 0.3-1.0 mg/ml. All cellular DNAs were sized by gel electrophoresis in 0.5% agarose gels. Uncut and restriction-cleaved λ DNAs were used as size markers.

EXAMPLE II

Culture and Identity of Cell Lines

NIH/3T3 (Janchill, et al., *J. Virol.*, 4, 549 (1969)) were maintained as monolayer cultures in Dulbecco's medium supplemented with penicillin (100 µg/ml) and streptomycin (100 µg/ml) and 10% bovine calf serum. The NIH/3T3 cells were not kept for longer than 2 months of continuous passage.

EXAMPLE III

Transfer of Genes capable of inducing Morphological Transformation utilized NIH/3T3 Cells as Recipients Precipitated cellular DNA (30 µg) in a volume of 1 ml was added to a 100 mm culture dish containing $2 \times 10^5$ to $6 \times 10^5$ cells in 10 ml of Dulbecco's medium and 10% calf serum. Cells were incubated at 37° C. in presence of the precipitate, which was removed after 8 to 12 hours. After an additional 12 to 24 hours, each plate of treated cells were trypsinized and seeded into three to five 100 mm dishes in Dublecco's medium and 5% calf serum. Cultures were re-fed with this medium at intervals of three to four days, until scoring of foci at days 14-21. 3T3 cultures fed with Dulbecco's medium and 5% calf serum do not maintain a confluent monolayer, so that the transformed foci eventually appear on a background of semiconfluent normal cells. Under these culture conditions, transformed focci are more clearly discernible, and the incidence of spontaneous focal overgrowths is lower than on cultures maintained in the same medium with 10% calf serum.

EXAMPLE IV

Generation of Secondary and Tertiary Transformants

Cultured cells, transformed by DNA treatment, were obtained from foci by cloning with use of glass cylinders. Such cultures were maintained in Dulbecco's medium supplemented with antibiotics and 5% bovine calf serum. The DNA were then purified by the method of Example Ib supra and the DNA thus obtained retransfected into NIH/3T3 cells in accordance to the method of Example III and the secondary transformants DNA therefrom again purified by the method of Example Ib supra and used to generate tertiary transformants as before.

EXAMPLE V

Cloning the Oncogenes from PR310 and PR371 Human Lung Tumors

A fragment of the oncogene of Calu-1 had been cloned previously by sonstructing complete genomic libraries in Charon 4A vectors by partially digesting DNA of an NIH/3T3 secondary transformant with EcoR1 and screening with the BLUR 8 clone containing human repetitive sequences. Overlapping fragments of the Calu-1 oncogene were isolated further by screening the libraries with restriction fragments contained in the first isolated phage, λ L2-3.4 (Shimizu, et al., PNAS, 80, 2112 (1983)).

We used a different approach for cloning the oncogenes from PR310 and PR371. DNA fragments of λ L2-3.4 were used to determine the position of contiquous restriction endonuclease sites located outside the cloned region of the oncogene by genomic blots of NIH/3T3 transformant DNAs. Once a restriction endonuclease fragment of a convenient size was found, it was cloned in appropriate phage vectors by complete digestion and size fractionation of mouse transformant DNAs.

Cellular NAs were cleaved with restriction endonucleases Hind III, Bam HI or Xba I (purchased from New England BioLabs and Bethesda Research Laboratories) according to suppliers' instructions.

Figure 2A:
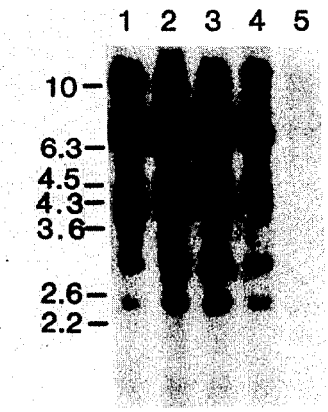
Figure 2B:
Figure 2C:
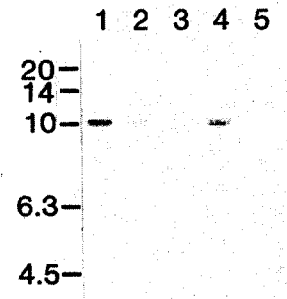

Thus, the 0.93-kbp EcoR1-Hind III fragment of λ L2-3.4 subcloned in pBR322 (pL-RH0.9) (FIG. 1a) was used in our initial cloning step to determine the position of the next Hind III site in the oncogene. We analyzed several NIH/3T3 transformants derived from DNAs of different human lung tumors. In all cases a 14-kbp Hind III fragment was found that hybridized with the probe (FIG. 2B). The 14-kbp Hind III fragment of NIH/3T3 tertiary transformant Ns-10 (FIG. 2B) derived from DNA of PR310 was cloned into the λ 47.1 vector by screening the library with pL-RH0.9 as described. From υ 150,000 recombinant phages constructed by in vitro packaging of the enriched 14-bkp Hind III fragment, 88 positive plaques were detected. The cloning procedure was thus simplified because it was sufficient to screen a lower number of phages from the partial libraries to obtain the other fragments of the oncogenes (see FIG. 1). For example, the 10-kbp Bam HI fragment located at 5' of the 14-kbp Hind III fragment was cloned from DNA of the N3-10 transformant into the λ 47.1 vector by using as probe the 0.25-kbp Hind III-Bam HI fragment fragment subcloned in pBR322 (pL-HB0.25) (FIGS. 1a and 2c). By screening 25,000 recombinant phage, 2 positive clones were identified. Cleaved DNA was subjected to electrophoresis through neutral 1% agarose gels (McDonell, et al., J. Mol. Biol. 110, 119 (1977)) and DNA was transferred to nitrocellulose by the method first described by Southern (J. Mol. Biol, 98, 503, (1975)).

Different fragments of DNA subcloned in plasmid vectors were labeled with 32p by nick translation (Maniatis, et al., PNAS 22, 1184, (1975)) with all four $\alpha$-$^{32}$p-dNTPs, to a specific activity of $2 \times 10^8$ dpm/ug. Hydridization was performed at a probe concentration of 5 ng/ml at 67° C. as previously described (Wigler, et al., Cell, 16, 115 (1979)). Filters were washed four times for 20 min each at 67° C. with 2×SSC (300 mM sodium chloride, 30 mM sodium citrate), 20 mM sodium phosphate, 0.06% sodium pyrophosphate and 0.05% SDS (pH 7.0) and one time in the same buffer, except with 1X SSC. After being blot-dried filters were exposed at −70° C. for 16 to 48 hours with Kodak XR-5 film with intensifying screens.

EXAMPLE VI

Defining the Boundaries of the Oncogenes

We analyzed the position of the next Hind III site located 5' of the oncogene by using as probe the 1.4-kbp Stu 1-Xba I fragment of λ LN-B10 subcloned into pchtk5 (pL-SX1.4) (FIG. 1). A 15-kbp Hind III fragment was observed in many transformants derived from different lung tumor DNAs (FIG. 2D) and in human normal and tumor DNA (data not shown). However, some of the NIH/3T3transformants showed a Hind III fragment of different sizes (lanes 1, 5, 11, 12 and 15), indicating that the 5' Hind III site was lost during the transfection cycles in these transformants. We concluded from this experiment that the cloning of this 15-kbp Hind III fragment should provide us with all of the essential sequences at the 5' end of the oncogene.

Figure 2D:
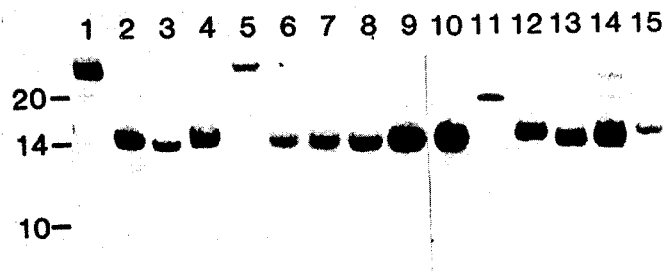

Two phages were isolated. λ LN-H16 and λ LD-H15 (FIG. 1) containing a 16-kbp and a 15-kbp Hind III fragment from the N2-4 and D2-2 transformants, respectively (FIG. 2D). Restriction mapping analysis revealed that the sequences present in these two phages were identical from the 3' Hind III site up to the SsT I site located 2 kbp upstream of the Bam HI site. However, from this site to the 5' end of the cloned sequences, the restriction map differed (FIG. 1).

Southern blot experiments using as probes the 2-kbp Sst I and the 3.5 kbp Hind III-Sst I fragments of λLD-H15 and λLN-H16, respectively (FIG. 1), showed that this region of the LD-H15 clone was of human origin, whereas the Hind III-Sst I fragment of LN-H16 contained mouse sequences, indicating that breakage of the oncogene occurred near the Sst I site in the N2-4 transformant (data not shown).

Figure 2E:
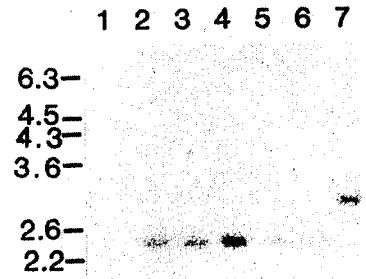

In a similar way, we found that the 3' EcoRI site of the 2.4-kbp EcoRI fragment present in λ L2-R7 was not retained in one secondary transformant derived from PR310 (FIG. 2E, lane 7). This difference in size was not due to an intrinsic difference in the structure of the oncogene from PR310 because other secondary transformants derived from this tumor retained the 2.4-kbp EcoRI fragment (FIG. 2E, lane 6). The 3' EcoRI site from the 1.1-kbp EcoRI fragment of λ L2-R7 also was not retained in some secondary and tertiary transformants (data not shown). These results suggest that the last 1.1-kbp EcoRI fragment present in λ L2-R7 is not an essential component of the oncogene. We conclude from these data that the size of the human c-K-ras oncogene must be 43–46 kbp.

EXAMPLE VII

Structure of the Oncogenes of PR310 and PR371

A composite partial restriction map of the human c-K-ras oncogene is detailed in FIG. 1. The cloned fragments of the oncogenes from Calu-1, PR310 and PR371 present identical restriction maps (with the exception of the sequences at the 5' end of the oncogene). The 0.9-kbp EcoRI-Hind III fragment of λ L-2-3.4 hybridized to a 14-kbp Hind III fragment and to a 6.8-kbp EcoRI fragment present in NIH/3T3 transformant DNAs derived from Calu-1, SK-LU-1, PR310, and PR371 DNAs as well as in the original tumor DNAs (FIG. 2B and data not shown). Similarly, the 0.25-kbp Hind III-Bam HI fragment of λLN-B10 hybridized to a 10-kbp Bam HI and a 4.6-kbp EcoRI fragment present in mouse transformant DNAs and in human DNA (FIG. 2C and data not shown). These results indicate that there are no additional Hind III fragments between the fragments cloned in our recombinant phages thus demonstrating the continuity of the cloned oncogene sequences.

EXAMPLE VIII

The Oncogenes of PR371 and PR310 contain Different Point Mutations in the Protein Coding Regions We have sequenced the first three exons of the PR310 and PR371 oncogenes. At position 12 of the predicted amino acid sequence of the first exon of the PR371 oncogene, a G→T transversion has resulted in the incorporation of cysteine instead of glycine as the 12th amino acid of the P21 protein of this oncogene (FIG. 3). The nucleotide sequence of the second and third exons of the PR371 oncogenes revealed no other changes relative to the reported sequences of these exons of the normal c-K-ras-2 allele (McGrath, et al., Nature, 304. 501 (1983)), and the Calu-1 oncogene (Shimizu, etal., Nature 304 497 (1983)).

The PR310 oncogene nucleotide sequence is normal in the first and third exons. This gene however contains a different point mutation at position 61 of the second coding exon. An A→T transversion at position 183 which corresponds to the third base of codon 61 results in the incorporation of histidine instead of glutamine in the predicted amino acid sequence of the P21 protein (FIG. 3).

EXAMPLE IX

Oncogenic Potential of the Mutations of PR371 and PR310 Oncogenes

Once the point mutation at position 61 of the second exon of the PR310 oncogene was detected by the sequence analysis, we constructed chimeric genes containing combinations of fragments of the c-K-ras and c-H-ras genes. The plasmids pLNHS 3.5 and pLDHS 3.5, containing the 2nd and 3rd exons of the PR310 and PR371 oncogenes respectively, were manipulated by conventional techniques of recombinant DNA to change the restriction site BalI, located 5' of the second exon, for a Hind III site, and the restriction site Stu-1, located between the 2nd and 3rd exons, for a XhoI site. (FIG. 4(A)). Similarly, the 4' Bal I site located between the 3rd and 4th exons of the plasmid XP2.1 which contain the last three exons of the c-H-ras gene from the T24 bladder carcinoma cell line, was changed to a BglII site.

The NdeI-XhoI DNA fragment, was purified after agarose gel electrophoresis of the plasmids carrying fragments of the PR310 and PR371 oncogenes. These fragments therefore contain the 2n exon of these oncogenes. Similarly, the XhoI-BglII DNA fragments which contain the 3rd exon of the two c-K-ras oncogenes were also purified as before.

Figure 4B:
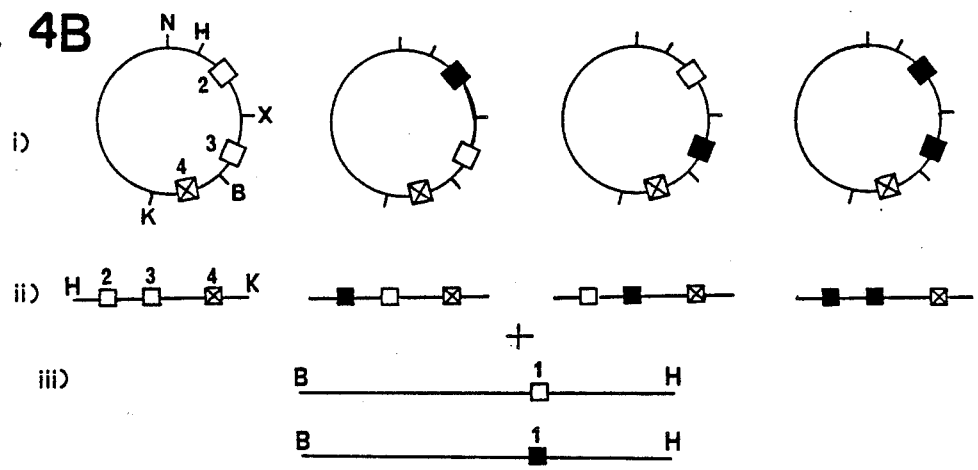
Figure 4C:
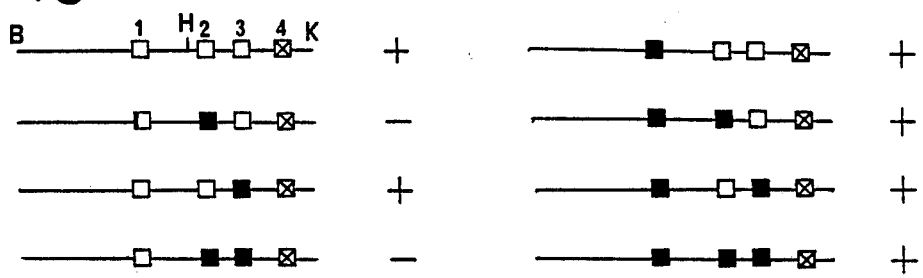

Using the NdeI-BglII DNA fragment purified from the manipulated PBXP2.1 plasmid, we constructed four different chimeric plasmids containing the 2nd and 3rd exon of the c-K-ras oncogenes, and the 4th exon of the c-H-ras oncogene, in all four possible combinations (FIG. 4(B)).

The Hind III-KpnI DNA fragments were purified from these chimeric plasmids, and ligated in vitro to the BglII-Hind III 14Kb fragments of the λLDH15 and λLNHI6 (see FIG. 4Biii) which contain the first exon of the PR371 and PR310 oncogenes respectively. The ligated DNA was used to transfect NIH/3T3 cells and foci of morphologically transformed cells scored after 14 days. The results are summarized in FIG. 4(C). Only the ligated DNA containing the 1st exon of the PR371 oncogene and/or the 2nd exon of the PR310 oncogene were able to transform the NIH 3T3. The combination containing the first exon of the PR310 oncogene and the second exon of the PR371 oncogene failed to induce morphological transformation in the NIH/3T3 cells, thus demonstrating that the mutation present in the second exon of PR310 oncogene was sufficient to confer oncogenic potential to the chimeric genes.

CONCLUSIONS

Because the only differences in the sequence of the first and second exons of PR310 and PR371 are the before mentioned base substitutions, these experiments demonstrate that:

1. The first exon of the PR371 oncogene and the second exon of the PR310 oncogene contain point mutations which confer transforming activity to the chimeric genes.
2. The first exon of the PR310 oncogene and the second exon of the PR71 oncogene do not contain any mutation, and therefore, chimeric genes containing these exons and other normal exons do not transform the NIH3T3.
3. The third exons of PR371 and PR310 oncogenes are normal in their predicted amino acid sequence.

Our results demonstrate that a P21 protein which contains a histidine at position 61 of the second exon, has potentiality to induce the oncogenic transformation of NIH/3T3 and Rat 2 and Rat 4 normal mouse and rat fibroblasts on culture, which is the conventional array to establish the functionality of human oncogenes.

EXAMPLE X

A 184 base pair Hinf I-Aha III fragment is excised from plasmid PLN-R3.0 containing the 2nd exon of PR310 oncogene. The fragment is ligated with Hind III linker following DNA polymerase I Klenow fragment repair of the Hinf I terminus, ligating with EcoRI linker, digesting with Hind III and EcoRI. The resulting EcoRI-Hind III fragment was inserted into the ECoRI-Hind III site of Pin III-A2 expression vector. (See FIG. 5).

The production of protein in E. coli with the constructed plasmid containing the mutation of amino acid No. 61 is done by the established methods (Masui, et al., Experim. Manipulation of Gene Expression, Academic Press, 15, 1983).

DETAILED DESCRIPTION OF THE DRAWINGS

FIG. 1a is a partial restriction map of the human C-K-ras oncogene. A composite restriction map of the c-K-ras oncogene activated in PR310, PR371 and Calu-1 human lung carcinomas was derived from the restriction maps of the DNA fragments cloned in overlapping or contiguous phage vectors. λ LN-H16 and λ LD-H15 are λ 47.1 Hind III derivatives constructed with DNA of NIH/3T3 secondary transformants N2-4 and D2-2 (see FIG. 2) derived from PR310 and PR371 tumor DNA, respectively. λ LN-B10 is a λ 47.1 Bam H1 recombinant from N3-10 tertiary transformants of PR310, PR371 and Calu-1 (FIG. 2) cloned into λ 47.1. λ LN-H10 and λ LD-H10 are recombinant λ 47.1 phages containing a 10.5-kbp Hind III fragment from N3-10 and D3-9 transformants, respectively. λ LN-X8 is a λ gtwes λ B derivative containing an 8.5-kbp Xba I fragment from N3-10 transformant. λ L2-3.4 and λ L2-R7 are Charon 4A clones containing sequences of a Calu-1-derived NIH/3T3 secondary transformant (Shimizu, et al., PNAS, 80, 2112 (1983)). The top of the figure shows maps of recombinant plasmids containing fragments of the oncogene sequences: pL-SX1.4 is the 1.4-kbp Stu 1-Xba 1 fragment of λLD-H15 cloned into the Sma 1-Xba 1 sites of pchtk2; pL-HB0.25 is a pBR322 derivative containing the 0.25-kbp Hind III-Bam H1 fragment of λ LN-H14; pL-R3.0, pL-R3.1 and pL-R2.4 are the 3.0-, 3.1 and 2.4-kbp EcoR1 fragments of λ LN-H14, λ L2-3.4, and λ L2-R7, respectively, cloned into the EcoR1 site of pBR322; and pL-RH0.9 is the 0.93-kbp EcoR1-Hind III fragment of λ L2-3.4 cloned into the EcoR1-Hind III site of pBR322. These plasmids were used as radioactive probes to screen the partial genomic libraries and to analyze the boundaries of the oncogene. Restriction endonuclease cleavage sites: B. BamH1; Bg. Bgl II: R, EcoR1: H, Hind III: P, PvU II; Sm, Sma1; S, Sst 1: X, XbaI: and Xn, Xho1. Location of the first four regions of the oncogenes hybridizing with the v-K-ras oncogene (clone HiHi3) (Ellis, et al., Nature, 292, 506 (1981)): ▨ position in the 4.8-kbp and 2.4-kbp EcoR1 fragments located at the 5' ar 3' ends of the oncogene, respectively, of two regions hybridizing with the viral clone pKBE-2 (Ellis, et al., 1981 ibid) but not with the clone HiHi3 ▓location of DNA fragments that contain Alu repeat sequence. The direction of transcription was determined by hybridization with specific restriction fragments of the v-K-ras clones.

FIG. 1b is a more detailed version of line B of FIG. 1.

FIG. 1c is a partial expansion of FIG. 1b, showing a partial expansion of the environments of the first four exons.

FIG. 2 is hybridization of NIH/3T3 mouse transformants DNA with human c-K-ras oncogene sequences, A,B, and C: DNA samples 6 µg each of NIH/3T3 (lanes 5), and NIH/3T3 tertiary transformants from PR310 (N3-10) (lanes 1). PR371 (D3-9) (lanes 2), Calu-1 (C3-4) (lanes 3), and SK-LU-1 (K3-5) (lanes 4), were digested with EcoR1 (A), Hind III (B), or Bam H1 (C) electrophoresed in 1% agarose gels, and analyzed by blot hybridization with $^{32}$p-labeled ($2 \times 10^8$ cpm/ug) BLUR 8 (A), pL-RH0.9 (B), and pL-HB0.25 (C) plasmids as probes. D: DNA samples (6 ug each) of NIH/3T3 secondary (lanes 2,4,7-10, 12 and 14) and tertiary (lanes 1,3,5,6,11,13 and 15) transformants from PR371 (lanes 1-4), SK-LU-1 (lanes 5-8), PR310 (lanes 9-12), and Calu-1 (lanes 13-15) were digested with Hind III, electrophoresed in 0.7 agarose gels, and analyzed before with $^{32}$P-labeled ($4 \times 10^8$ cpm/ug) pL-SX1.4 as probe. Tertiary and secondary transformants of human lung tumors PR371 and PR310, respectively D3-9 (lane 1), D2-2 (lane 4), N3-10 (lane 11), and N2-4 (lane 12). E: NIH/3T3 (lane 1) and NIH/3T3 tertiary transformant (lanes 2-7) DNA (6 ug each) from PR371 (lanes 2 and 3), SK-LU-1 (lane 4), Calu-1 (lane 5), and PR310 (lanes 6 and 7) were digested with EcoR1, and the presence of sequences hybridizing with pL-R2.4 were analyzed as before. Transfer to nitrocellulose filters and hydridization with nick-translated probes was performed as described (Perucho, et al., Cell, 27, 467 (1981)). The position and molecular weights in kbp of adenovirus 2 DNA BamH1 and e,ums/Eco/ R1 fragments are indicated at the left of the figures.

FIG. 3 represents the nucleotide 3 sequence of the first three exons of the C-K-ras oncogene of PR310 and PR371 tumors. The nucleotide sequence of the viral Kirsten oncogene (Tushida, et al., Science, 217, 937 (1982)) is also represented for comparative purposes. The corresponding sequence of amino acids of the encoded P21 proteins is also represented. The points in the nucleotide sequence represent identical nucleotides and the asterisks indicate identical amino acids. The arrows indicate the location of the splicing signals which define the boundaries of the exons.

The sequence was determined by the method of Maxam-Gilbert (Methods of Enzymol. 65, 499 (1980)), using sequencing strategies based in the previously determined restriction map of the oncogene (FIG. 1).

FIG. 4 represents the construction of plasmids carrying chimeric genes containing combinations of exons of the c-K-ras and c-H-ras oncogenes.

(A) pLNSH 3.5 and pLDSH 3.5 are recombinant plasmids containing the Sst-1-Hind III and 3.5 Kb fragment of λLNH14 and λLDH14 respectively (FIG. 1). PBXP 2.1 is the XbaI-Pvu II 2.1 Kb fragment of the plasmid PTB-1 (Goldfarb, et al., Nature, 296, 404 (1982) containing the last three normal exons of the T24 c-H-ras oncogene, cloned into the XbaI-SmaI sites of pchtk-2, a plasmid containing the chicken tk gene (Perucho, et al., Nature, 285, 207 (1980)). These plasmids were manipulated to change the restriction sites indicated Bas=- Bal I was changed to a H=Hind III; S=Stu-I was changed to a X=XhoI; and Ba=Bal I was changed to a B=BglII site. N=NdeI; Xb=XbaI; Ss=Sst-I; K=KpnI.

(B) The indicated different restriction fragments were purified by agarose gel electrophoresis and used to prepare the four different recombinant plasmids. The Hind III-KpnI fragments were purified as above from the recombinant plasmids, and ligated in vitro to the BglII-Hind III 14Kb fragment of λLNH16 and λLDH15, containing the first exon of PR310 and PR371 oncogenes respectively.

(C) The ligated DNA was used to transform NIH/3T3 cells as previously described and the foci scored after 14 days.

The open squares represent exons of PR310 c-K-ras oncogene; the black squares represent exons of PR371 oncogene and the crossed squares represent exons of the T24 c-H-ras oncogene.

We claim:

1. Purified DNA from a human c-K ras gene capable of transforming NIH3T3 mouse fibroblast cells to tumorigneic cells, said DNA containing a mutation in codon 61 of the second exon thereof.

2. Purified DNA of claim 1 wherein the c-K ras gene is derived from the human lung carcinoma line PR 310 (ATCC CRL- 8477).

3. Purified DNA of claim 1 wherein the mutation is a transversion in said codon 61.

4. Purified DNA of claim 3 wherein the transversion is in the third base of said codon 61.

5. Purified DNA of claim 4 wherein the transversion is an A→T transversion.

6. Purified DNA comprising the nucleotide sequence:

```
ATG ACT GAA TAT AAA CTT GTG GTA GTT GGA GCT GGT GGC GTA GGC
AAG AGT GCC TTG ACG ATA CAG CTA ATT CAG AAT CAT TTT GTG GAC
GAA TAT GAT CCA ACA ATA GAG GAT TCC TAC AGG AAG CAA GTA GTA
ATT GAT GGA GAA ACC TGT CTC TTG GAT ATT CTC GAG ACA GCA GGT
CAT GAG GAG TAC AGT GCA ATG AGG GAC CAG TAC ATG AGG ACT GGG
GAG GGC TTT CTT TGT GTA TTT GCC ATA AAT AAT ACT AAA TCA TTT
GAA GAT ATT CAC CAT TAT AGA GAA CAA ATT AAA AGA GTT AAG GAC
TCT GAA GAT GTA CCT ATG GTC CTA GTA GGA AAT AAA TGT GAT TTG
CCT TCT AGA ACA GTA GAC ACA AAA CAG GCT CAG GAC TTA GCA AGA
AGT TAT GGA ATT CCT TTT ATT GAA ACA TCA GCA AAG ACA AGA CAG
```

7. Purified DNA of claim 1 having the partial nucleotide sequence of the second coding exon.

8. Purified DNA of claim 2 having the partial nucleotide sequence of the second coding exon.

9. Purified DNA of claim 6 having the partial nucleotide sequence of the second coding exon.

10. A cloning vector containing the DNA of claim 1.

11. The cloning vector of claim 10 which is a bacterial plasmid or bacteriophage.

12. The cloning vector of claim 11 which is a pBR322 plasmid.

13. A cloning vector containing the DNA of claim 2.

14. The cloning vector of claim 13 which is a bacterial plasmid or bacteriophage.

15. The cloning vector of claim 14 which is a pBR322 plasmid.

16. A cloning vector containing the DNA of claim 6.

17. The cloning vector of claim 16 which is a bacterial plasmid or bacteriophage.

18. The cloning vector of claim 17 which is a pBR322 plasmid.

* * * * *